United States Patent
May et al.

(10) Patent No.: US 11,426,209 B2
(45) Date of Patent: Aug. 30, 2022

(54) SPINAL IMPLANT SYSTEM AND METHODS OF USE

(71) Applicant: WARSAW ORTHOPEDIC INC., Warsaw, IN (US)

(72) Inventors: Jason M. May, Collierville, TN (US); William A. Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 129 days.

(21) Appl. No.: 16/787,645

(22) Filed: Feb. 11, 2020

(65) Prior Publication Data

US 2020/0170681 A1   Jun. 4, 2020

Related U.S. Application Data

(62) Division of application No. 15/216,483, filed on Jul. 21, 2016, now Pat. No. 10,575,878.

(51) Int. Cl.
*A61B 17/70*   (2006.01)

(52) U.S. Cl.
CPC ................ *A61B 17/7038* (2013.01)

(58) Field of Classification Search
CPC ............ A61B 17/7038; A61B 17/7037; A61B 17/7035
See application file for complete search history.

(56) References Cited

U.S. PATENT DOCUMENTS

| | | | | |
|---|---|---|---|---|
| 2007/0161996 A1* | 7/2007 | Biedermann | ...... | A61B 17/7037 606/305 |
| 2008/0243185 A1* | 10/2008 | Felix | .................. | A61B 17/7037 606/246 |
| 2009/0198280 A1* | 8/2009 | Spratt | ................ | A61B 17/7038 606/267 |
| 2011/0106173 A1* | 5/2011 | Lindemann | ........ | A61B 17/7038 606/302 |
| 2011/0178559 A1* | 7/2011 | Barry | ................. | A61B 17/8605 606/305 |
| 2013/0110176 A1* | 5/2013 | Rezach | .............. | A61B 17/7038 606/305 |
| 2013/0226243 A1* | 8/2013 | Kraus | ................ | A61B 17/7037 606/264 |
| 2014/0046374 A1* | 2/2014 | Asaad | ................ | A61B 17/7049 606/267 |

* cited by examiner

*Primary Examiner* — Julianna N Harvey
(74) *Attorney, Agent, or Firm* — Sorell, Lenna & Schmidt, LLP

(57) ABSTRACT

A spinal implant includes a first member having an inner surface defining an implant cavity and at least one mating element. A second member includes a head and a shaft configured to penetrate tissue. The head includes at least one mating element engageable with the at least one mating element of the first member and a part. A third member includes an inner surface engageable with the part such that the members comprise a bone fastener having a selected movement. Systems, instruments and methods are disclosed.

17 Claims, 11 Drawing Sheets

SPINAL IMPLANT SYSTEM AND METHODS OF USE

CROSS-REFERENCE TO RELATED APPLICATIONS

This application is a divisional application of U.S. patent application Ser. No. 15/216,483, filed on Jul. 21, 2016, which is hereby incorporated by reference herein, in its entirety.

TECHNICAL FIELD

The present disclosure generally relates to medical devices for the treatment of spinal disorders, and more particularly to a spinal implant system including a bone fastener.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a spinal implant is provided. The spinal implant includes a first member having an inner surface defining an implant cavity and at least one mating element. A second member includes a head and a shaft configured to penetrate tissue. The head includes at least one mating element engageable with the at least one mating element of the first member and a part. A third member includes an inner surface engageable with the part such that the members comprise a bone fastener having a selected movement. In some embodiments, systems, instruments and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
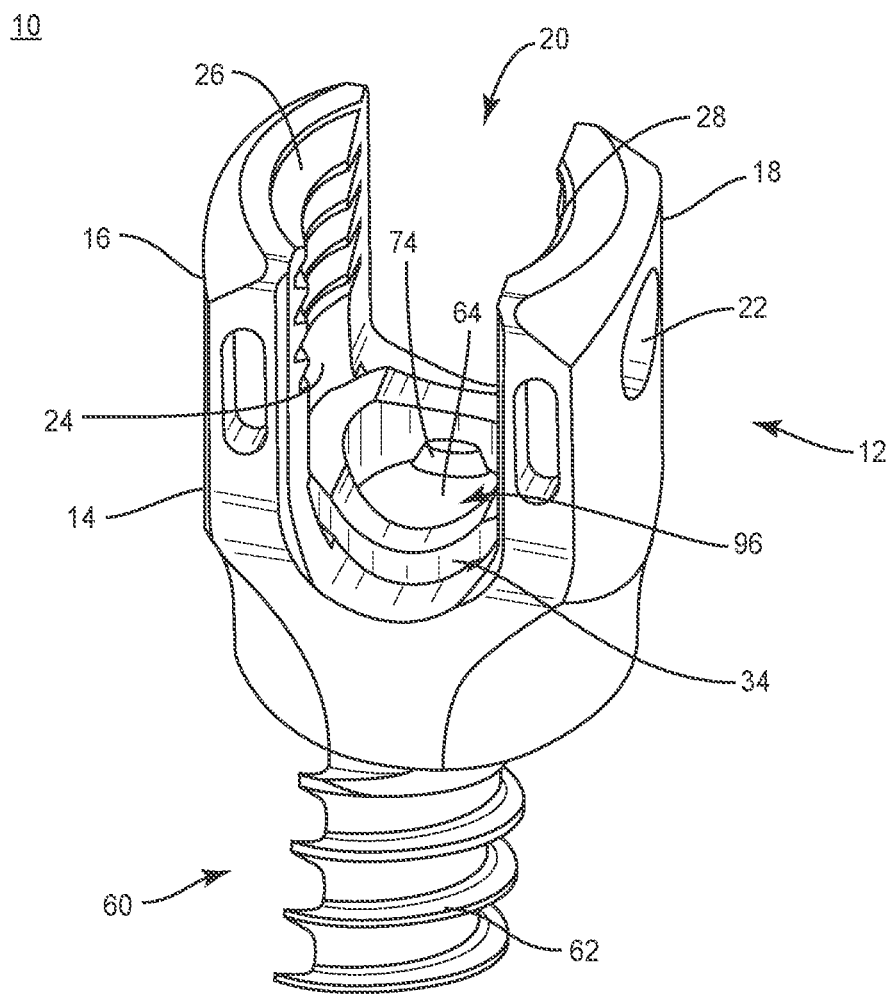
FIG. 1 is a perspective view of components of one embodiment of a spinal implant system in accordance with the principles of the present disclosure.
Figure 2:
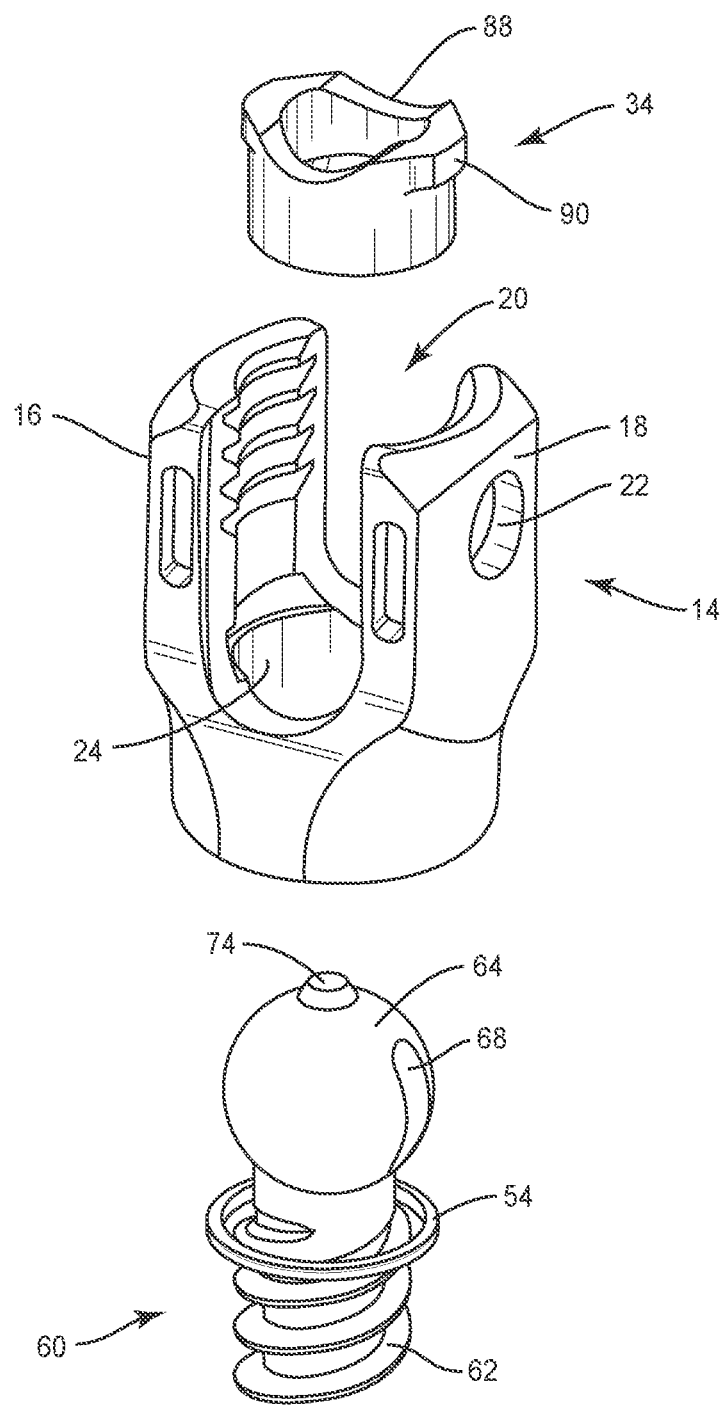
FIG. 2 is a perspective view of the components shown in FIG. 1 with parts separated.

The exemplary embodiments of a surgical system and related methods of use disclosed are discussed in terms of medical devices for the treatment of musculoskeletal disorders and more particularly, in terms of a spinal implant system including a bone fastener.

In some embodiments, the spinal implant system comprises a modular system including an array of members, such as, for example, one or more crowns configured for selective movement of a bone fastener, as described herein. In some embodiments, the spinal implant system comprises a bone screw including an interface portion, such as, for example, a groove. In some embodiments, the groove is engaged with a receiver such that the receiver applies a torque to drive the bone screw. In some embodiments, connection of the receiver and the bone screw provides multi-axial motion while also allowing for torque transmission to drive the bone screw. In some embodiments, engagement of the bone screw and the receiver forms a swivel drive bone fastener.

In some embodiments, the bone screw includes a top surface configured to control the functionality of the bone screw. In some embodiments, the top surface includes a protrusion configured to interface with a crown. In some embodiments, the crowns are interchangeable to facilitate multi-axial, uni-axial, fixed-angle, or other functionality within the same bone screw assembly. In some embodiments, the crown members include alternate embodiments of inserts configured for engagement with a pre-loaded crown to change the functionality.

In some embodiments, the crown insert is configured to allow for transverse motion of the bone screw in a first orientation and prevent motion in a selected plane in a second orientation by rotating the crown insert. In some embodiments, this feature facilitates utilization in scoliosis applications in which rod capture is in a transverse plane initially but then motion needs to be locked to facilitate derotation.

In some embodiments, the spinal implant system allows for modular crowns providing various bone screw functionality within a pedicle screw. In some embodiments, the functionality may be changed in-situ, on the operating room back table, or at the manufacturing facility.

In some embodiments, the spinal implant system includes a swivel drive concept for bone fasteners. In some embodiments, the head of the bone screw includes a spherical configuration. In some embodiments, the head of the bone screw includes a protrusion configured to interface with an opening of a crown member to provide a multi-axial screw (MAS), uni-axial screw (URS) or fixed-angle screw (FAS). In some embodiments, the bone screw head does not include a socket drive feature.

In some embodiments, the bone screw head includes a driving groove. In some embodiments, the receiver includes a driving protrusion. In some embodiments, the driving protrusion is configured to facilitate multi-axial functionality between the receiver and the bone screw. In some embodiments, the protrusion disposed on the bone screw head is configured to limit angular motion of the bone screw relative to the receiver. In some embodiments, the driving protrusion and the driving groove form a swivel drive interface.

In some embodiments, the crown provides for multi-axial movement of the bone screw relative to the receiver. In some embodiments, the crown provides for uni-axial movement of the bone screw relative to the receiver. In some embodiments, the crown provides for a fixed-angle of the bone screw relative to the receiver.

In some embodiments, the spinal implant system includes a modular swivel drive. In some embodiments, the spinal implant system is employed with a method of assembly of the bone fastener that includes the crown having flanges, such as, for example, wings configured to align with a rod slot of the receiver. In some embodiments, the crown is configured for engagement with the receiver and the bone screw. In some embodiments, the crown is configured for rotation, such as, for example, a quarter turn relative to the receiver to fix the crown with the receiver.

In some embodiments, the spinal implant system is employed with a method of assembly of the bone fastener that includes pre-loading a MAS crown with the receiver. In some embodiments, the spinal implant system includes a crown insert. In some embodiments, the crown insert includes a uni-axial crown or a fixed-angle crown. In some embodiments, the method includes aligning the wings with a rod slot of the receiver. In some embodiments, the crown insert is configured for disposal with a MAS crown. In some embodiments, the crown insert is configured for rotation, such as, for example, a quarter turn relative to the MAS crown to fix the crown insert with the receiver.

In some embodiments, the spinal implant system includes a swivel drive uni-axial configuration. In some embodiments, the uni-axial crown includes an opening, such as, for example, a slot configured to facilitate translation of the bone screw in a transverse plane. In some embodiments, this configuration facilitates rod capture in a scoliosis case. In some embodiments, a method of utilizing the uni-axial crown includes rotating the uni-axial crown after rod capture to align the slot in a sagittal plane. In some embodiments, disposal of the crown slot in the sagittal plane is configured to resist and/or prevent transverse translation to facilitate derotation.

In some embodiments, one or all of the components of the surgical system are disposable, peel-pack, pre-packed sterile devices. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-8, there are illustrated components of a spinal implant system 10 including a plurality of alternate bone fastener configurations, such as, for example, a plurality of bone fastener configurations 12.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 comprises a spinal implant, such as, for example, a bone fastener 12. In some embodiments, spinal implant system 10 comprises a spinal implant kit, which includes a plurality of members, such as, for example, a plurality of alternate crowns that includes at least one crown 34. Crown 34 is configured for selection from the plurality of crowns such that crown 34 is assembled with a member, such as, for example, a receiver 14 and a member, such as, for example, a screw 60 to provide bone fastener 12 with multi-axial functionality, as described herein. In some embodiments, the plurality of crowns may include crowns having configurations alternate to crown 34, which provide, for example, alternate functionality to bone fastener 12, for example, uni-axial or fixed axis functionality.

Receiver 14 extends along and defines an axis X1. Receiver 14 includes a pair of spaced apart arms 16, 18 that define an implant cavity 20 therebetween configured for disposal of a component of a spinal construct, such as, for example, a spinal rod (not shown). Arms 16, 18 each extend parallel to axis X1. In some embodiments, arm 16 and/or arm 18 may be disposed at alternate orientations, relative to axis X1, such as, for example, transverse, perpendicular and/or other angular orientations such as acute or obtuse, coaxial and/or may be offset or staggered. Arms 16, 18 each include an arcuate outer surface extending between a pair of side surfaces. At least one of the outer surfaces and the side surfaces of arms 16, 18 have at least one cavity, such as, for example, a recess 22. Recesses 22 are configured for engagement with a surgical instrument, such as, for example, a driver (not shown) to drive and/or rotate bone fastener 12, as described herein.

Cavity 20 is substantially U-shaped. In some embodiments, all or only a portion of cavity 20 may have alternate cross section configurations, such as, for example, closed, V-shaped, W-shaped, oval, oblong triangular, square, polygonal, irregular, uniform, non-uniform, offset, staggered, and/or tapered. Receiver 14 includes an inner surface 24. A portion of surface 24 includes a thread form 26 located adjacent arm 16 and a thread form 28 located adjacent arm 18. Thread forms 26, 28 are each configured for engagement with a coupling member, such as, for example, a setscrew (not shown), to retain a spinal construct, such as, for example, a spinal rod (not shown) within cavity 20. In some embodiments, surface 24 may be disposed with the coupling member in alternate fixation configurations, such as, for example, friction fit, pressure fit, locking protrusion/recess, locking keyway and/or adhesive. In some embodiments, all or only a portion of surface 24 may have alternate surface configurations to enhance engagement with the spinal rod and/or a setscrew such as, for example, rough, arcuate, undulating, mesh, porous, semi-porous, dimpled and/or textured.

Receiver 14 includes a surface 30 that defines a cavity, such as, for example, a slot 32. Slot 32 is configured to receive a flange of crown 34, as described herein. Slot 32 includes surfaces 32*a*, 32*b*. In some embodiments, all or only a portion of surface 30 may have alternate surface configurations to enhance engagement with crown 34, such as, for example, rough, arcuate, undulating, mesh, porous, semi-porous, dimpled and/or textured.

Figure 3:
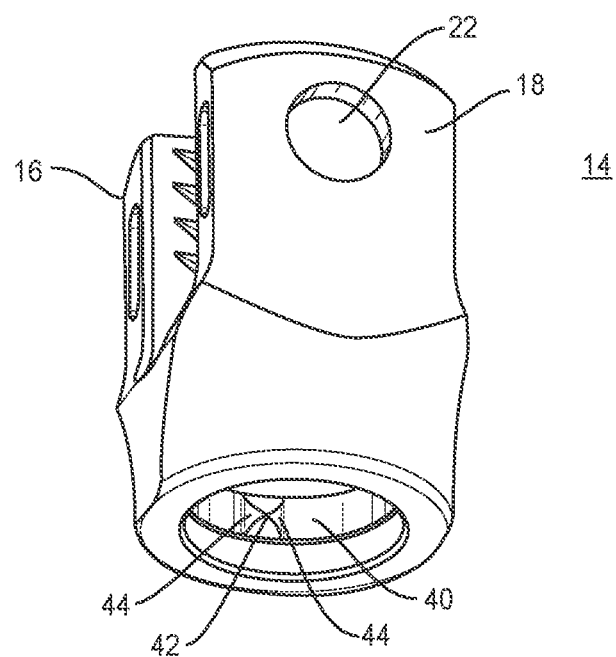
FIG. 3 is a perspective view of components of the system shown in FIG. 1.
Figure 7:
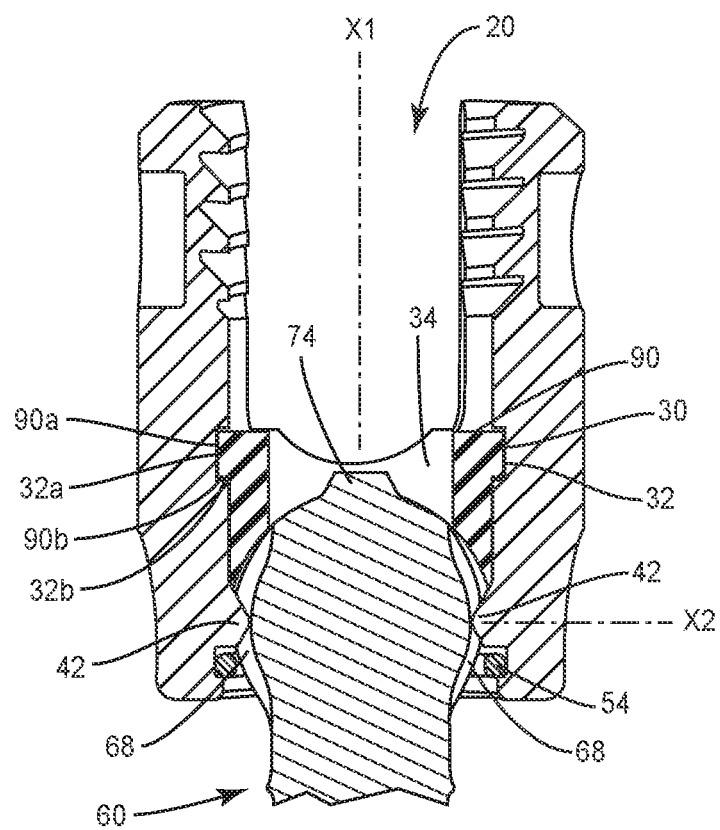
FIG. 7 is a cross section view of the components shown in FIG. 1.

Receiver 14 includes a surface 40, as shown in FIG. 3. Surface 40 includes mating elements, such as, for example, a pair of protrusions 42, as shown in FIG. 7. Protrusions 42 extend laterally from surface 40. In some embodiments, protrusions 42 are aligned with an axis X2. In some embodiments, axis X2 is disposed transverse relative to axis X1. In some embodiments, axis X2 may be disposed at alternate orientations, relative to axis X1, such as, for example, perpendicular and/or other angular orientations such as acute or obtuse, coaxial and/or may be offset or staggered. Protrusions 42 include surfaces 44 that are configured to slide and/or translate relative to a portion of a head 64 of screw 60 to facilitate multi-axial movement of receiver 14 relative to screw 60, as described herein. In some embodiments, protrusions 42 are configured to engage a surface of head 64 to apply a torque to head 64 causing the interface between receiver 14 and head 64 to rotate screw 60, for example, to penetrate tissue, as described herein. In some embodiments, this configuration replaces a socket feature disposed with head 64.

Figure 6:
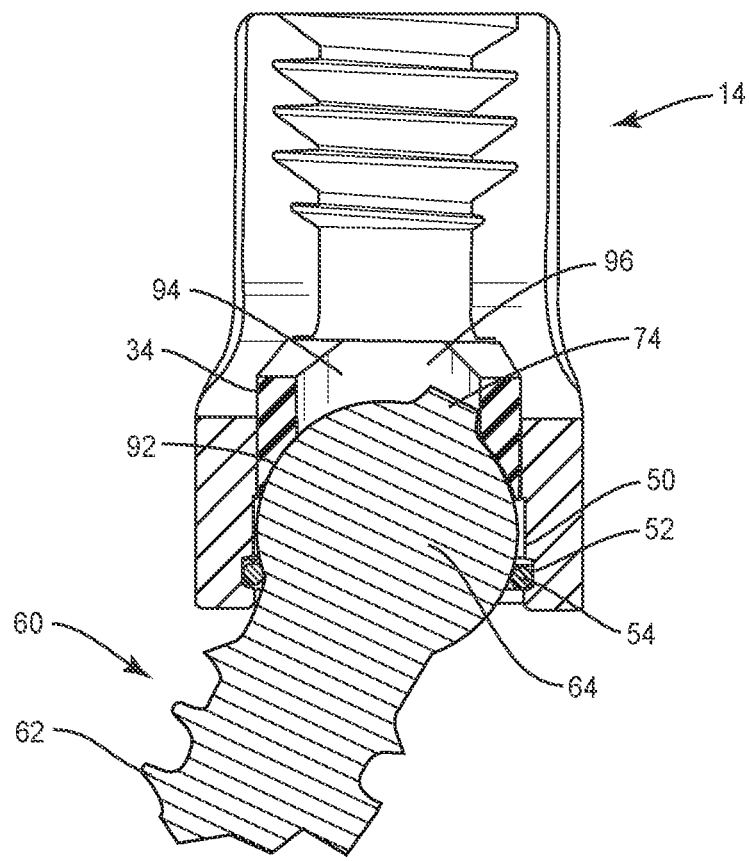
FIG. 6 is a cross section view of the components shown in FIG. 1.

Receiver 14 includes a surface 50. Surface 50 defines a cavity, such as, for example, a groove 52 configured for disposal of a band, such as, for example, a ring 54, as shown in FIG. 6. In some embodiments, ring 54 includes a C-shaped configuration. Ring 54 is configured to engage an outer surface of head 64 and is disposable with groove 52 to resist and/or prevent axial translation of shaft 62 relative to receiver 14 and facilitate rotation of shaft 62 relative receiver 14. In some embodiments, ring 54 is disposed within head 64 to enhance a retaining strength of bone fastener 12 and resist and/or prevent shearing of shaft 62.

Figure 4:
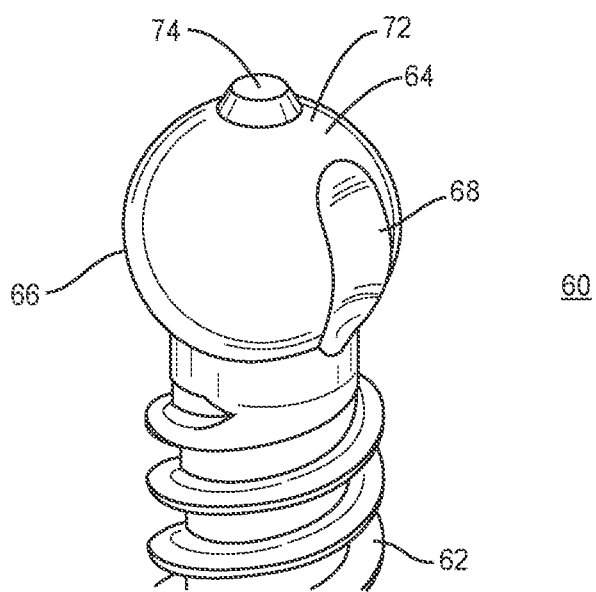
FIG. 4 is a perspective view of components of the system shown in FIG. 1.

Spinal implant system 10 includes screw 60, which includes a shaft 62 and head 64, as shown in FIG. 4. Shaft 62 is configured to penetrate tissue, such as, for example, bone. Head 64 is configured for selected movement relative to receiver 14 and crown 34, as described herein. Head 64 includes a surface 66. Surface 66 includes mating elements, such as, for example, a pair of longitudinal grooves 68. Grooves 68 extend axially along surface 66 such that grooves 68 are substantially parallel to axis X1 and may be cut radially around the center of the sphere. In some embodiments, grooves 68 may be disposed at alternate orientations, relative to axis X1, such as, for example, perpendicular and/or other angular orientations such as acute or obtuse, coaxial and/or may be offset or staggered. In some embodiments, grooves 68 include an oblong configuration. In some embodiments, grooves 68 may have alternate cross section configurations, such as, for example, oval, triangular, square, polygonal, irregular, uniform, non-uniform, offset, staggered, and/or tapered. In some embodiments, head 64 may include one or a plurality of mating elements disposed at the same or alternate relative orientations.

Figure 8:
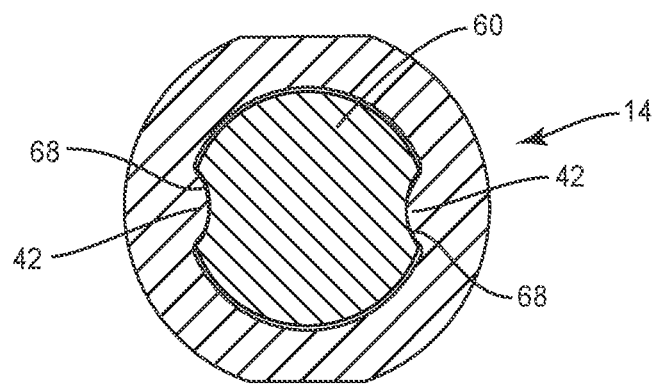
FIG. 8 is a cross section view of the components shown in FIG. 1.

Grooves 68 are disposed in a spaced apart configuration along surface 66. Grooves 68 are configured for a mating engagement with protrusions 42, as shown in FIG. 8. Surfaces 44 of protrusions 42 are configured to slide and/or translate within and relative to surface 66 to facilitate relative rotation and/or pivoting of receiver 14 and screw 60 upon disposal in a selected plane or axis to facilitate multi-axial movement of bone fastener 12. In some embodiments, protrusions 42 are configured to engage surface 66 to apply a torque to screw 60. The torque applied to head 64 causes receiver 14 to rotate screw 60 for selected orientation of receiver 14/screw 60 and/or fixation with bone, as described herein.

Head 64 includes a part, such as, for example, a surface 72. In some embodiments, surface 72 includes a protrusion 74 extending from head 64. Protrusion 74 is configured for engagement with crown 34 to define a selected movement and/or range of movement of bone fastener 12, as described herein. Protrusion 74 is configured for rotation relative to crown 34 to provide the selected movement and/or range of movement. Protrusion 74 is configured to limit the selected movement by engagement with a surface of crown 34, as described herein. In some embodiments, the part includes surface 72 having an even, spherical configuration. In some embodiments, head 64 includes one or a plurality of parts disposed at the same or alternate relative orientations, and/or having alternate configurations, as described herein.

In some embodiments, the components of spinal implant system 10 include a spinal implant kit, which comprises receivers 14, screws 60 and interchangeable crowns 34. The plurality of crowns include crowns 34 and alternate crowns, such as those described herein, that interface with receiver 14 to comprise one or more bone fastener configurations.

In some embodiments, receiver 14 is connected to a selected crown 34 to comprise a multi-axial receiver. In some embodiments, receiver 14 is connected to a selected crown 34 to comprise a uni-axial receiver. In some embodiments, receiver 14 is connected to a selected crown 34 to comprise a fixed axis receiver to resist and/or prevent movement of shaft 62 relative to receiver 14. In some embodiments, receiver 14 comprises one or more fixed axis receivers, multi-axial receivers and uni-axial receivers. In some embodiments, spinal implant system 10 comprises a spinal implant kit, which includes alternate crowns, such as those described herein. In some embodiments, spinal implant system 10 comprises a spinal implant kit, which includes alternate receivers, screws and crowns.

Figure 5:
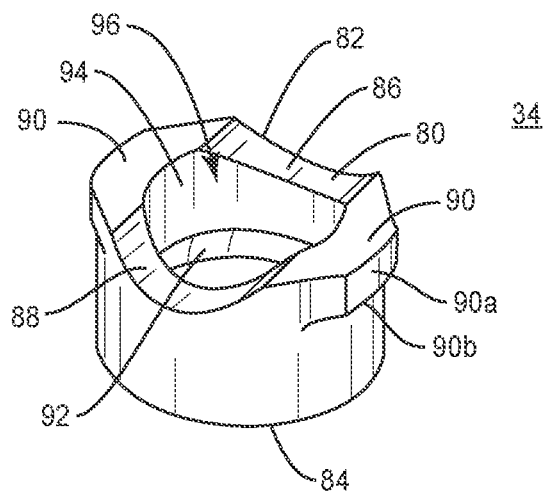
FIG. 5 is a perspective view of components of the system shown in FIG. 1.

A selected crown 34 is configured for disposal within cavity 20 of receiver 14. Each crown 34 includes a wall 80 having an end surface 82 and an end surface 84, as shown in FIG. 5. Surface 82 is configured to define at least a portion 86 of cavity 20. Portion 86 is defined by an outer surface 88 that defines a curved portion of crown 34 configured for engagement with a spinal rod. In some embodiments, all or only a portion of surface 88 may have alternate cross section configurations, such as, for example, oval, oblong triangular, square, polygonal, irregular, uniform, non-uniform, offset, staggered, and/or tapered.

Surface 82 defines a flange 90 configured for mating engagement with slot 32 of receiver 14. Flange 90 includes surfaces 90*a*, 90*b*. In some embodiments, crown 34 is rotated relative to receiver 14 for fixation with receiver 14. Rotation of crown 34 causes slot 32 to retain crown 34 within receiver 14. In some embodiments, flange 90 is initially aligned with a rod slot and rotated, such as, for example, substantially 90 angular degrees and/or a quarter turn to engage slot 32. In some embodiments, flange 90 can be rotated in a range of 0 through 360 angular degrees for engagement and connection with receiver 14. In some embodiments, flange 90 engages the surface of slot 32 in a keyed connection such that surface 90*a* abuts surface 32*a* and surface 90b abuts surface 32b. In some embodiments, engagement of flange 90 and slot 32 prevents rotation and/or axial translation of crown 34 relative to surface 30 of receiver 14.

Surface 84 defines an engagement portion 92 configured for engagement with head 64, as described herein. Engagement portion 92 of crown 34 is concave or semi-spherical to accommodate the substantially spherical configuration of head 64 such that head 64 is rotatable relative to receiver 14. This configuration allows shaft 62 to be rotatable relative to axis X1 through one or a plurality of planes. Crown 34 includes a surface 94 that defines an opening 96. Opening 96 is disposed in communication with cavity 20. Head 64 is configured for moveable disposal within opening 96 such that rotation of head 64 relative to receiver 14 and/or crown 34 causes protrusion 74 to engage surface 94 to define and/or limit the relative motion of receiver 14/screw 60 including pivoting or rotation, and the selected movement of bone fastener 12, for example, multi-axial movement. In some embodiments, shaft 62 is connected to receiver 14 to comprise a multi-axial fastener 12.

Engagement of head 64 with crown 34 defines a selected movement of its components parts and/or movement relative to tissue. In some embodiments, the selected movement includes rotation and/or pivotal movement of shaft 62 relative to receiver 14 about one or a plurality of axes. In some embodiments, shaft 62 is relatively rotatable and/or pivotable, as described herein, to a selected angle through and within an angular range in a plurality of planes. In some embodiments, the angular range is 0 to 360 degrees. In some embodiments, the selected movement includes rotation and/or pivotal movement of shaft 62 relative to receiver 14 through one or a plurality of planes. In some embodiments, shaft 62 is connected to a selected receiver 14 to comprise a multi-axial fastener 12. In some embodiments, spinal implant system 10 comprises a spinal implant kit, which includes alternate receivers and crowns having various angular ranges, such as those described herein.

In assembly, operation and use, spinal implant system 10, similar to the systems and methods described herein, includes a selected bone fastener 12, which comprises a pedicle screw having a selected crown 34 for connection with receiver 14 and screw 60 having a selected movement and/or range of movement, and is employed with a surgical procedure for treatment of a spinal disorder affecting a section of a spine of a patient, as discussed herein. In some embodiments, crown 34 is selected and interchangeable with receiver 14 and/or screw 60, in-situ or on a back table of an operating room during a surgical procedure, or at a manufacturing facility.

In one embodiment, a crown 34 is selected from the kit of the plurality of crowns 34 for connection with receiver 14 and screw 60 to comprise a bone fastener 12 having multi-axis movement and/or MAS functionality. Screw 60 is assembled with receiver 14. Translation of receiver 14 relative to head 64 causes ring 54 to engage groove 52 of receiver 14. Ring 54 is configured to engage an outer surface of head 64 and is disposable with groove 52 to resist and/or prevent axial translation of shaft 62 relative to receiver 14 and facilitate rotation of shaft 62 relative receiver 14, as described herein. Protrusions 42 are disposed with grooves 68 facilitating rotating and/or pivoting of receiver 14 relative to screw 60, as described herein.

Figures 9, 10, 11:
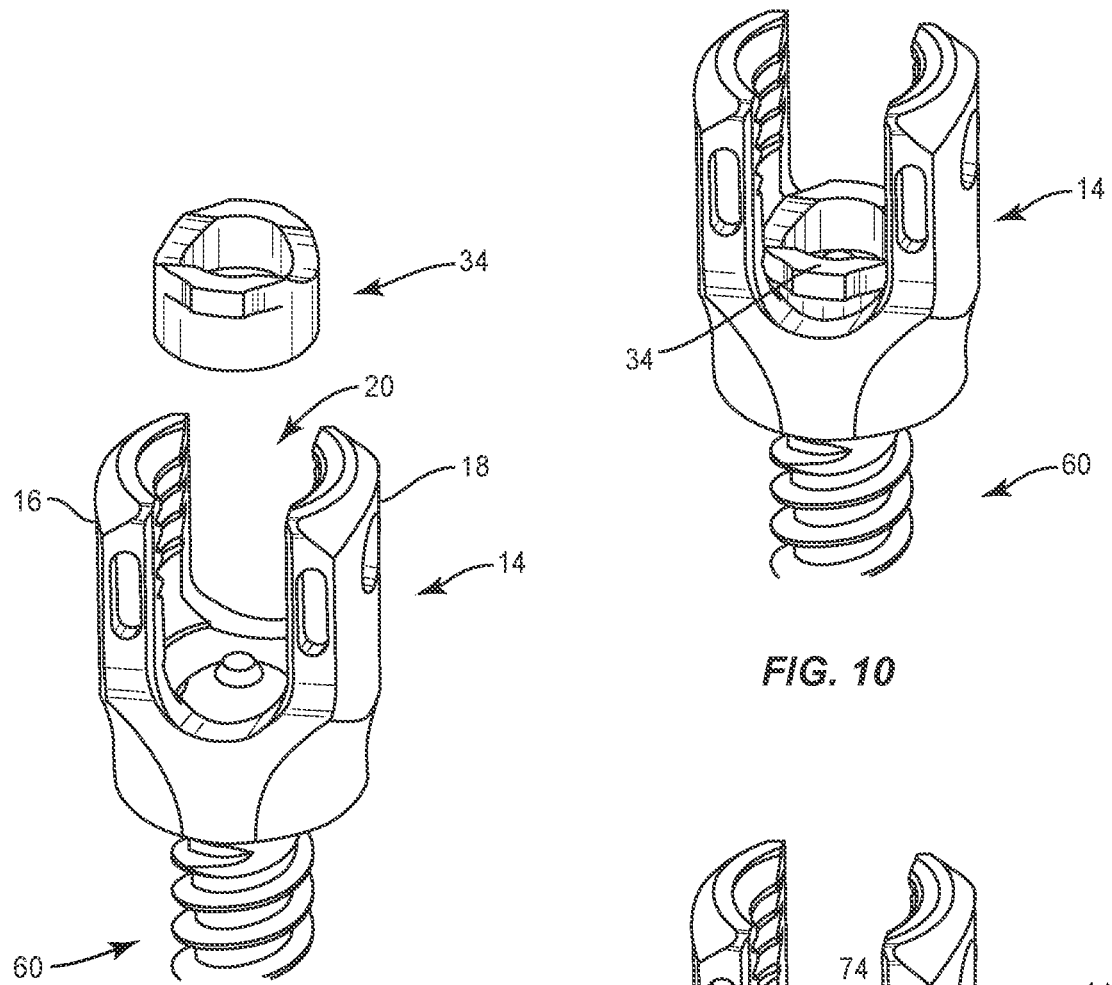
FIG. 9 is a break away perspective view of the components shown in FIG. 1.
FIG. 10 is a break away perspective view of the components shown in FIG. 1.
FIG. 11 is a break away perspective view of the components shown in FIG. 1.
Figure 12:
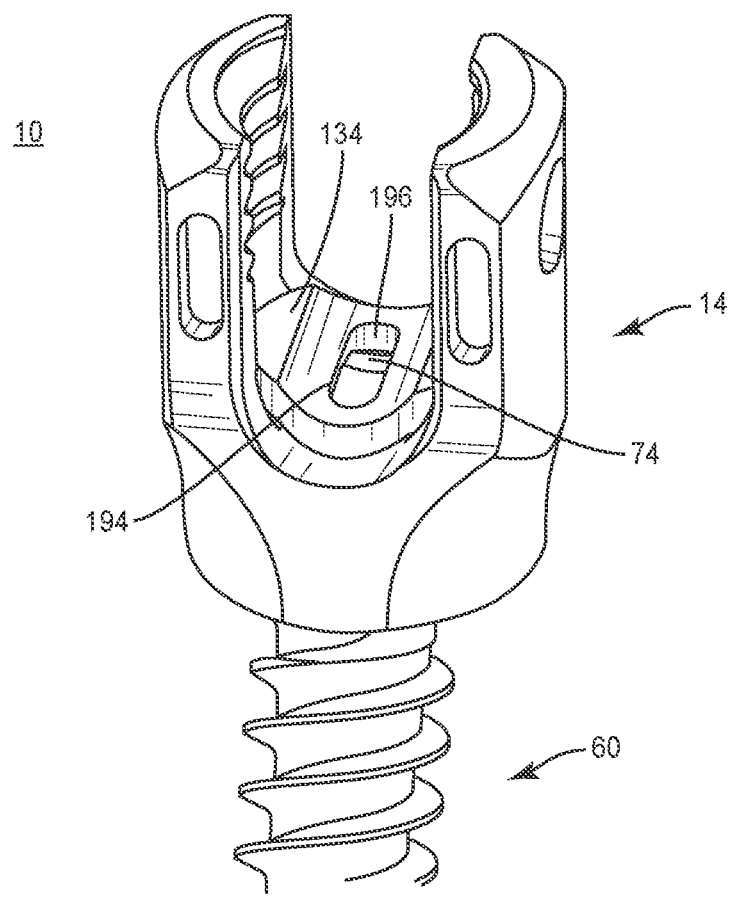
FIG. 12 is a perspective view of components of one embodiment of a spinal implant system in accordance with the principles of the present disclosure.

A selected crown 34, having a selected movement configuration, is disposed with cavity 20 of receiver 14 to comprise a bone fastener 12, for example, having multi-axial movement and/or MAS functionality. Crown 34 is disposed with receiver 14 such that flange 90 extends between arms 16, 18 and is in alignment with the rod slot, as shown in FIG. 9. Crown 34 is engaged with head 64. Crown 34 is rotated, such as, for example, substantially 90 angular degrees and/or a quarter turn clockwise or counterclockwise to engage flange 90 with slot 32. Rotation of crown 34 causes crown 34 to be retained within receiver 14. Surface 88 is positioned in cavity 20 to receive a spinal rod (not shown).

Screw 60 pivots, rotates and/or swivels relative to receiver 14, such as, for example, by rotation and/or pivoting along a plurality of axes and/or within a plurality of planes of vertebrae to provide multi-axis orientation and/or MAS functionality. Rotation of screw 60 relative to receiver 14 facilitates orientation relative to tissue including bone. Protrusion 74 limits movement to the selected movement of screw 60 relative to receiver 14 by engaging surface 94 as screw 60 rotates within opening 96, as described herein.

A surgical instrument, such as, for example, a driver (not shown) is engaged with recesses 22. Upon connection of the driver with receiver 14, the driver is rotated, such that rotation of the driver and the interface of protrusions 42 and surface 66 provide a driving torque to fasten bone fastener 12 with vertebral tissue including bone. Upon engagement of bone fastener 12 with the vertebral tissue, receiver 14 is pivotable through an angular range of 0-360 degrees relative to axis X1 to facilitate positioning of receiver 14 to capture a spinal rod. Upon placement and positioning of bone fastener 12, a spinal rod is disposed with cavity 20. A coupling member is utilized to secure the spinal rod with bone fastener 12.

In use, for treatment of a spinal disorder, shaft 62 can be threaded and engaged with tissue. In some embodiments, the bone fastener 12 is disposed adjacent vertebrae at a surgical site and is manipulated to drive, torque, insert or otherwise connect bone fastener 12 with vertebrae.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments the agent may be HA coating. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In some embodiments, spinal implant system 10 can include one or a plurality of bone fasteners 12 such as those described herein and/or fixation elements, which may be employed with a single vertebral level or a plurality of vertebral levels. In some embodiments, bone fasteners 12 may be engaged with vertebrae in various orientations, such as, for example, series, parallel, offset, staggered and/or alternate vertebral levels. In some embodiments, bone fasteners 12 may be configured as multi-axial screws, sagittal angulation screws, pedicle screws, mono-axial screws, uniplanar screws, fixed screws, anchors, tissue penetrating screws, conventional screws, expanding screws. In some embodiments, bone fasteners 12 may be employed with wedges, anchors, buttons, clips, snaps, friction fittings, compressive fittings, expanding rivets, staples, nails, adhesives, connectors, fixation plates and/or posts.

In one embodiment, as shown in FIGS. 12-15, spinal implant system 10, similar to the systems and methods described herein, comprises a spinal implant kit, which includes a plurality of members, such as, for example, a plurality of alternate crowns that includes at least one crown 134, similar to crown 34 described herein. Crown 134 is selectable from the plurality of crowns such that crown 134 is employed with receiver 14 and screw 60 to provide bone fastener 12 with uni-axial functionality, as described herein. In some embodiments, the plurality of crowns may include crowns having configurations alternate to crown 134, which provide, for example, alternate functionality to bone fastener 12, for example, multi-axial or fixed axis functionality.

Figure 13:
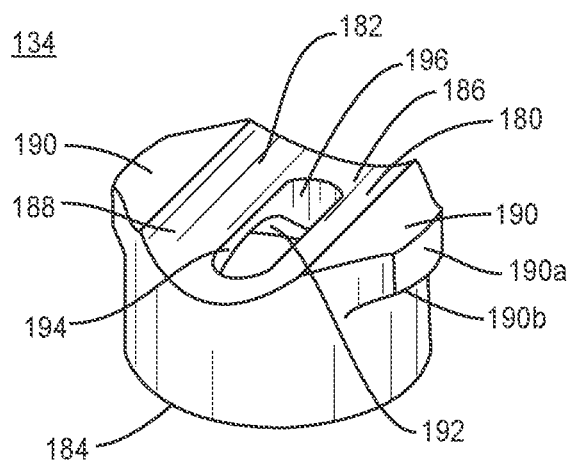
FIG. 13 is a perspective view of components of the system shown in FIG. 12.

Crown 134 is configured for disposal within cavity 20 of receiver 14. Crown 134 includes a wall 180 having an end surface 182 and an end surface 184, as shown in FIG. 13. Surface 182 is configured to define at least a portion 186 of cavity 20. Portion 186 is defined by an outer surface 188 that defines a curved portion of crown 134 configured for engagement with a spinal rod.

Surface 182 defines a flange 190 configured for mating engagement with slot 32 of receiver 14, similar to that described herein. Flange 190 includes surfaces 190*a*, 190*b*. In some embodiments, crown 134 is rotated relative to receiver 14 for fixation with receiver 14. Rotation of crown 134 causes slot 32 to retain crown 134 within receiver 14. In some embodiments, flange 190 is initially aligned with a rod slot and rotated, such as, for example, substantially 90 angular degrees and/or a quarter turn to engage slot 32. In some embodiments, flange 190 can be rotated in a range of 0 through 360 angular degrees for engagement and connection with receiver 14. In some embodiments, flange 190 engages the surface of slot 32 in a keyed connection such that surface 190*a* abuts surface 32*a* and surface 190*b* abuts surface 32*b*. In some embodiments, engagement of flange 190 and slot 32 prevents rotation and/or axial translation of crown 134 relative to surface 30 of receiver 14.

Surface 184 defines an engagement portion 192 configured for engagement with head 64, as described herein. Engagement portion 192 of crown 134 is concave or semispherical to accommodate the substantially spherical configuration of head 64 such that head 64 is rotatable relative to receiver 14. Crown 134 includes a surface 194 that defines a linear opening or slot 196. This configuration allows shaft 62 to be rotatable relative to axis X1 through a selected and/or single plane. Slot 196 is disposed in communication with cavity 20. Head 64 is configured for moveable disposal within slot 196 such that rotation of head 64 relative to receiver 14 and/or crown 134 causes protrusion 74 to engage surface 194 to define and/or limit the relative motion of receiver 14/screw 60 including pivoting or rotation, and the selected movement of bone fastener 12, for example, uniaxial movement. In some embodiments, shaft 62 is connected to receiver 14 to comprise a uni-axial fastener 12.

Engagement of head 64 with crown 134 defines a selected movement of its components parts and/or movement relative to tissue. In some embodiments, the selected movement includes movement of screw 60 in a single plane relative to receiver 14. In this configuration, shaft 62 is free to rotate along a single axis and/or within a single plane relative to receiver 14, similar to a fastener having uni-axial functionality.

Figure 14:
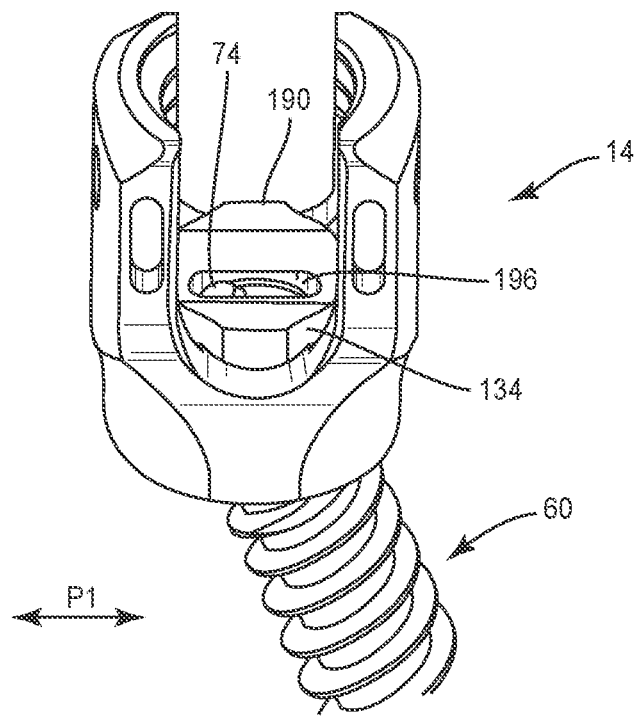
FIG. 14 is a perspective view of components of the system shown in FIG. 12.

In assembly, operation and use, spinal implant system 10, similar to the systems and methods described herein, includes a selected bone fastener 12, which comprises a selected crown 134 for connection with receiver 14 and screw 60 having a selected movement and/or range of movement, and is employed with a surgical procedure for treatment of a spinal disorder affecting a section of a spine of a patient, as discussed herein. In some embodiments, crown 34 is selected and interchangeable with receiver 14 and/or screw 60, in-situ or on a back table of an operating room during a surgical procedure, or at a manufacturing facility. A selected crown 34 is disposed with receiver 14 such that flange 190 extends between arms 16, 18 and is in alignment with the rod slot, as shown in FIG. 14. Crown 134 is engaged with head 64. In this configuration, positioning of crown 134 facilitates movement of screw 60 in a first plane, such as, for example a transverse plane P1, as shown in FIG. 14.

Figure 15:
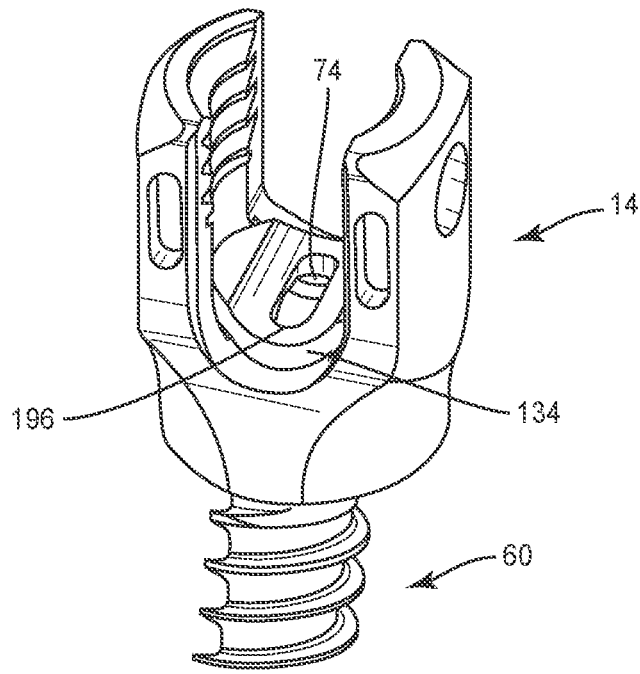
FIG. 15 is a perspective view of components of the system shown in FIG. 12.

Crown 134 is rotated, such as, for example, substantially 90 angular degrees and/or a quarter turn clockwise or counterclockwise to engage flange 190 with slot 32, as shown in FIG. 15. Rotation of crown 134 causes crown 134 to be retained within receiver 14. Surface 188 is positioned in cavity 20 to receive a spinal rod (not shown). In some embodiments, receiver 14 and crown 134 capture the spinal rod such that movement in transverse plane P1 is resisted and/or prevented to fix the spinal rod with bone fastener 12 in a surgical procedure to treat, for example, scoliosis, and facilitate derotation of vertebrae.

Figure 16:
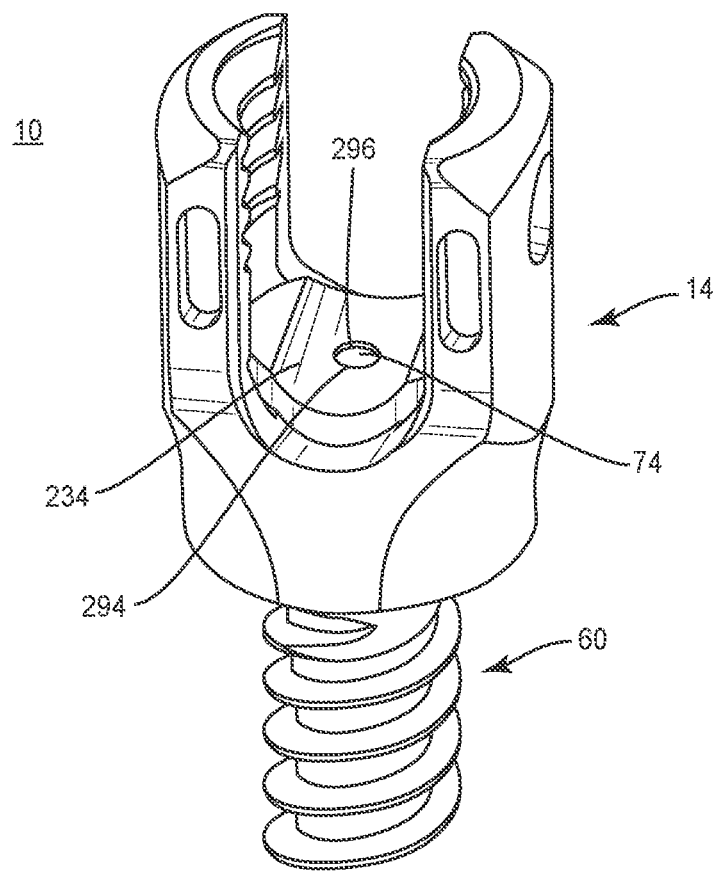
FIG. 16 is a perspective view of components of one embodiment of a spinal implant system in accordance with the principles of the present disclosure.
Figure 17:
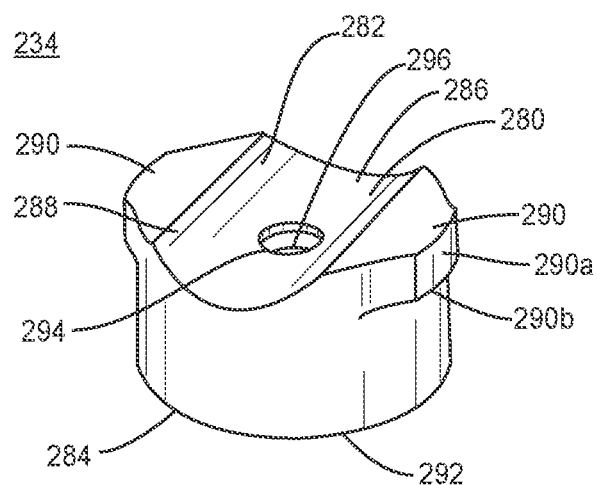
FIG. 17 is a perspective view of components of the system shown in FIG. 16.
Figure 18:
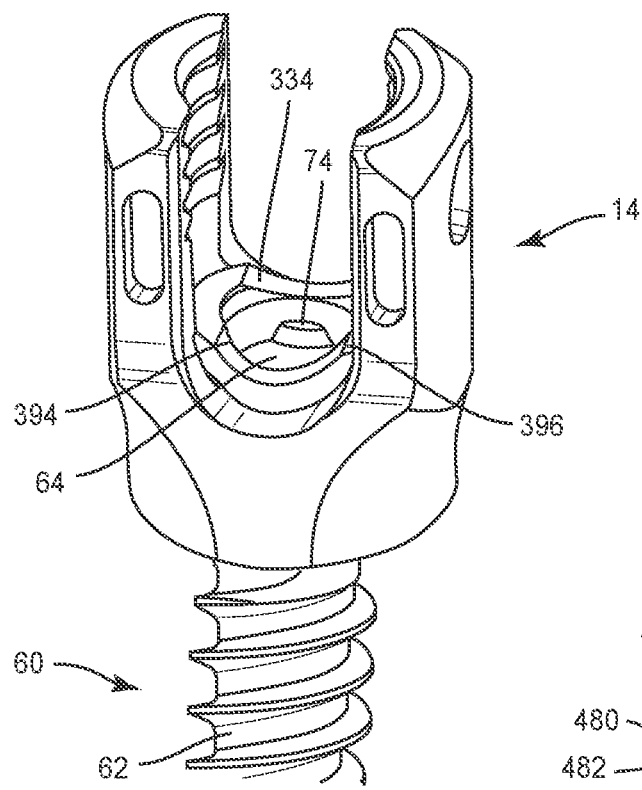
FIG. 18 is a perspective view of components of one embodiment of a spinal implant system in accordance with the principles of the present disclosure.

In one embodiment, as shown in FIGS. 16 and 17, spinal implant system 10, similar to the systems and methods described herein, comprises a spinal implant kit, which includes a plurality of members, such as, for example, a plurality of alternate crowns that includes at least one crown 234, similar to the crowns described herein. Crown 234 is configured for selection from the plurality of crowns such that crown 234 is employed with receiver 14 and screw 60 to provide bone fastener 12 with fixed-axis functionality, as described herein. In some embodiments, the plurality of crowns may include crowns having configurations alternate to crown 234, which provide, for example, alternate functionality to bone fastener 12, for example, multi-axial or uni-axial functionality.

Crown 234 is configured for disposal within cavity 20 of receiver 14. Crown 234 includes a wall 280 having an end surface 282 and an end surface 284, as shown in FIG. 17. Surface 282 is configured to define at least a portion 286 of cavity 20. Portion 286 is defined by an outer surface 288 that defines a curved portion of crown 234 configured for engagement with a spinal rod.

Surface 282 defines a flange 290 configured for mating engagement with slot 32 of receiver 14. Flange 290 includes surfaces 290*a*, 290*b*. In some embodiments, crown 234 is rotated relative to receiver 14 for fixation with receiver 14. Rotation of crown 234 causes slot 32 to retain crown 234 within receiver 14. In some embodiments, flange 290 is initially aligned with a rod slot and rotated, such as, for example, substantially 90 angular degrees and/or a quarter turn to engage slot 32. In some embodiments, flange 290 can be rotated in a range of 0 through 360 angular degrees for engagement and connection with receiver 14. In some embodiments, flange 290 engages the surface of slot 32 in a keyed connection such that surface 290*a* abuts surface 32*a* and surface 290*b* abuts surface 32*b*. In some embodiments, engagement of flange 290 and slot 32 prevents rotation and/or axial translation of crown 234 relative to surface 30 of receiver 14.

Surface 284 defines an engagement portion 292 configured for engagement with head 64, as described herein.

Engagement portion 292 of crown 234 is concave or semi-spherical to accommodate the substantially spherical configuration of head 64. Crown 234 includes a surface 294 that defines an opening 296. Opening 296 is disposed in communication with cavity 20. Protrusion 74 is configured for disposal within opening 296 such that rotation and/or pivoting of head 64 relative to receiver 14 and/or crown 134 is resisted and/or prevented. As such, protrusion 74 engages surface 294 to define the configuration and/or movement of bone fastener 12 as a fixed axis fastener.

Engagement of head 64 with crown 234 defines a selected movement of its components parts and/or movement relative to tissue. In some embodiments, the selected movement includes resisting and/or preventing movement of shaft 62 relative to receiver 14, axially and/or planar to provide bone fastener 12 with fixed-axis functionality.

In one embodiment, as shown in FIGS. 18-21, spinal implant system 10, similar to the systems and methods described herein, comprises a spinal implant kit, which includes a crown 334, similar to the crowns described herein, and a plurality of alternate inserts that includes at least one insert 434. Crown 334 and insert 434 are configured for selection from the plurality of crowns and inserts such that crown 334 and insert 434 are employed with receiver 14 and screw 60 to provide bone fastener 12 with uni-axial functionality, as described herein. In some embodiments, the kit may include crowns and/or inserts having configurations alternate to crown 334 and/or insert 434, which provide, for example, alternate functionality to bone fastener 12, for example, multi-axial or fixed axis functionality.

Crown 334, similar to crown 34, is configured for disposal within cavity 20 of receiver 14. Crown 334 includes a surface 394 that defines an opening 396. Opening 396 is disposed in communication with cavity 20. Head 64 is configured for moveable disposal within opening 396 such that rotation of head 64 relative to receiver 14 and/or crown 334 causes protrusion 74 to engage surface 394 to define and/or limit the relative motion of receiver 14/screw 60 including pivoting or rotation to a multi-axial movement of bone fastener 12.

Crown 334 includes a surface 400 that defines a slot 402. Slot 402 is configured to receive a flange of an insert 434, as described herein. Slot 402 includes surfaces 402*a*, 402*b*. In some embodiments, the plurality of inserts include insert 434 and alternate inserts, which interface with crown 334 to comprise one or more bone fastener configurations to provide for a second selected movement of bone fastener 12. In some embodiments, a selected insert 434 is connected to crown 334 to comprise a uni-axial bone fastener 12. In some embodiments, a selected insert 434 is connected to crown 334 to comprise a fixed axis bone fastener 12 to resist and/or prevent movement of shaft 62 relative to receiver 14.

Figure 19:
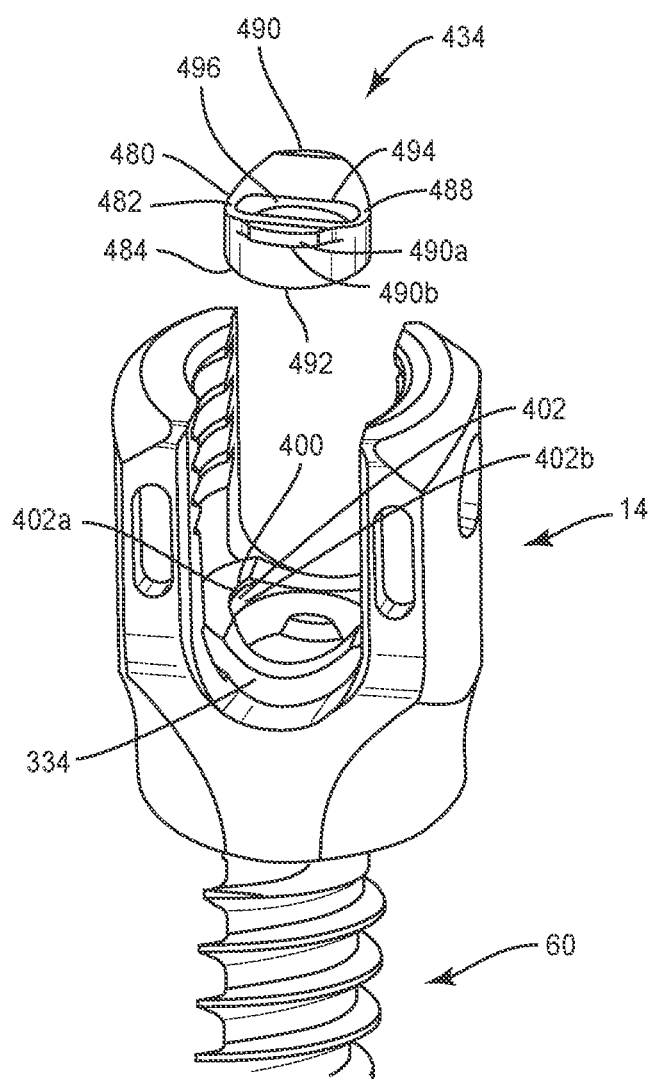
FIG. 19 is a perspective view of the components shown in FIG. 18 with parts separated.
Figure 20:
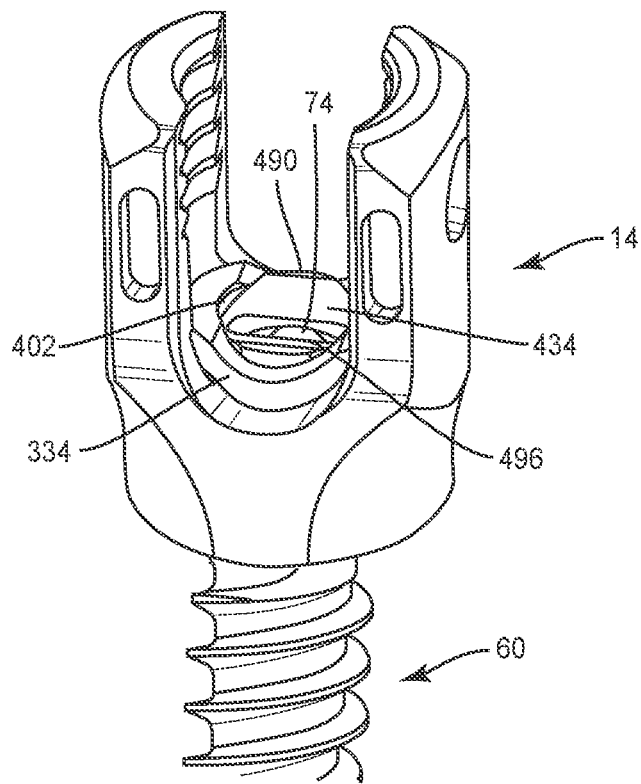
FIG. 20 is a perspective view of components of the system shown in FIG. 18.
Figure 21:
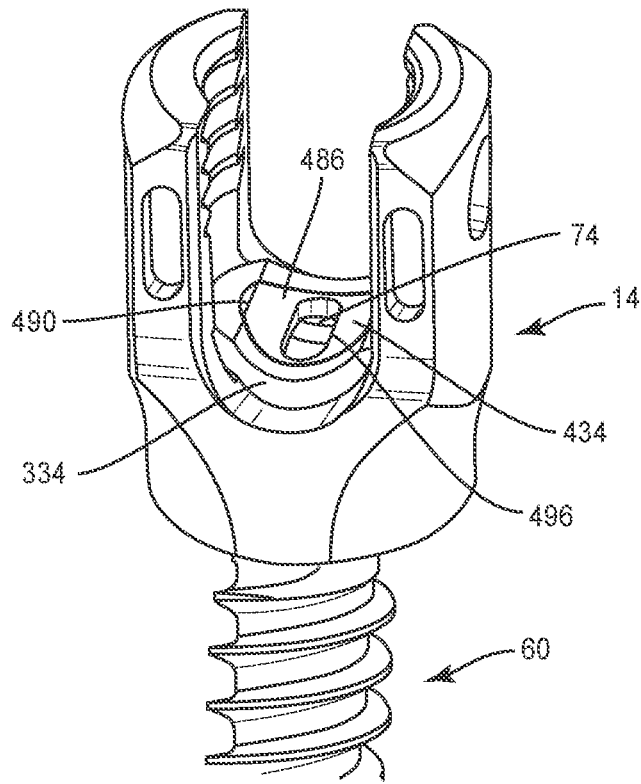
FIG. 21 is a perspective view of components of the system shown in FIG. 18.

A selected insert 434 is configured for disposal within cavity 20 of receiver 14 and opening 396 of crown 334. Insert 434 includes a wall 480 having an end surface 482 and an end surface 484, as shown in FIG. 19. Surface 482 is configured to nest within crown 334 to define at least a portion 486 of cavity 20, as shown in FIG. 21. Portion 486 is defined by an outer surface 488 that defines a curved portion of insert 434 configured for engagement with a spinal rod. In some embodiments, all or only a portion of surface 488 may have alternate cross section configurations, such as, for example, oval, oblong triangular, square, polygonal, irregular, uniform, non-uniform, offset, staggered, and/or tapered.

Surface 482 defines a flange 490 configured for mating engagement with slot 402 of crown 334. Flange 490 includes surfaces 490*a*, 490*b*. In some embodiments, insert 434 is rotated relative to crown 334 for fixation with crown 334. Rotation of insert 434 causes slot 402 to retain insert 434 within crown 334 and receiver 14. In some embodiments, flange 490 is initially aligned with a rod slot and rotated, such as, for example, substantially 90 angular degrees and/or a quarter turn to engage slot 402. In some embodiments, flange 490 can be rotated in a range of 0 through 360 angular degrees for engagement and connection with receiver 14. In some embodiments, flange 490 engages the surface of slot 402 in a keyed connection such that surface 490*a* abuts surface 402*a* and surface 490*b* abuts surface 402*b*. In some embodiments, engagement of flange 490 and slot 402 prevents rotation and/or axial translation of insert 434 relative to surface 30 of receiver 14 and/or crown 334.

Surface 484 defines an engagement portion 492 configured for engagement with head 64, as described herein. Engagement portion 492 of insert 434 is concave or semi-spherical to accommodate the substantially spherical configuration of head 64 such that head 64 is rotatable relative to receiver 14, similar to that described herein. Crown 434 includes a surface 494 that defines a linear opening or slot 496. This configuration allows shaft 62 to be rotatable relative to axis X1 through a selected and/or single plane. Slot 496 is disposed in communication with cavity 20. Head 64 is configured for moveable disposal within slot 496 such that rotation of head 64 relative to receiver 14, crown 334 and/or insert 434 causes protrusion 74 to engage surface 494 to define and/or limit the relative motion of receiver 14/screw 60 including pivoting or rotation, and the selected movement of bone fastener 12, for example, uni-axial movement.

Engagement of head 64 with insert 434 defines a selected movement of its components parts and/or movement relative to tissue. In some embodiments, shaft 62 is connected to receiver 14 to comprise a uni-axial fastener. In some embodiments, the selected movement includes movement in a single plane relative to receiver 14. In this configuration, shaft 62 is free to rotate along a single axis and/or within a single plane relative to receiver 14, similar to a fastener having uni-axial functionality.

In assembly, operation and use, spinal implant system 10, similar to the systems and methods described herein, includes a selected bone fastener 12, which comprises a selected crown 334 and a selected insert 434 for connection with receiver 14 and screw 60 having a selected movement and/or range of movement, and is employed with a surgical procedure for treatment of a spinal disorder affecting a section of a spine of a patient, as discussed herein. In some embodiments, crown 334 and insert 434 are selected and interchangeable with receiver 14 and/or screw 60, in-situ or on a back table of an operating room during a surgical procedure, or at a manufacturing facility.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A spinal implant comprising:
 a first member including an inner surface defining an implant cavity, the first member including a pair of lateral protrusions;

a second member including a head and a shaft configured to penetrate tissue, the head including a pair of longitudinal grooves, each of the grooves including one of the protrusions disposed therein, the second member including an extension extending from the head;

a third member directly engaging the first and second members, the third member defining an opening, the extension being disposed in the opening to restrict movement of the second member relative to the first member, and a circumferential ring;

wherein the inner surface of the first member defines a groove and the circumferential ring is disposed in the groove such that the ring engages an outer surface of the head.

2. A spinal implant as recited in claim 1, wherein the lateral protrusions are aligned with a transverse axis of the first member.

3. A spinal implant as recited in claim 1, wherein the longitudinal grooves are spaced about an outer surface of the second member.

4. A spinal implant as recited in claim 1, wherein the first member comprises a slot extending into the inner surface and the third member comprises a flange, the flange being received in the slot.

5. A spinal implant as recited in claim 1, wherein the protrusions include surfaces, the surfaces of the protrusions being configured to translate relative to the head to facilitate multi-axial movement of the first member relative to the second member.

6. A spinal implant as recited in claim 1, wherein:
the lateral protrusions are aligned with a transverse axis of the first member;
the longitudinal grooves are spaced about an outer surface of the second member, the grooves being defined by a surface of the second member; and
the protrusions are configured to translate within and relative to the surface of the second member to facilitate relative rotation of the first member and the second member upon disposal in a selected plane or axis to facilitate multi-axial movement of the spinal implant.

7. A spinal implant as recited in claim 1, wherein:
the lateral protrusions are aligned with a transverse axis of the first member;
the longitudinal grooves are spaced about an outer surface of the second member, the grooves being defined by a surface of the second member; and
the protrusions are configured to engage the surface of the second member to apply torque to the head such that the torque applied to the head causes the second member to rotate the first member.

8. A spinal implant as recited in claim 1, wherein the shaft defines an axis, the extension being coaxial with the axis.

9. A spinal implant as recited in claim 1, wherein the extension is movably disposed within the opening such that rotation of the second member relative to the first member causes the protrusion to engage the inner surface of the third member to limit multi-axial movement of the first member relative to the second member.

10. A spinal implant as recited in claim 1, wherein a distal end of the third member directly engages proximal ends of the protrusions to prevent axial translation of the third member relative to the first member in one direction.

11. A spinal implant as recited in claim 1, wherein the first member comprises a slot extending into the inner surface and the third member comprises a flange, the flange being received in the slot such that opposite proximal and distal surfaces of the flange directly engage surfaces of the first member that define the slot.

12. A spinal implant as recited in claim 1, wherein the first member is monolithic and includes a body and spaced apart arms extending proximally from the body, the head extending through an opening in the body.

13. A spinal implant as recited in claim 1, wherein the shaft defines an axis, the extension being coaxial with the axis, the extension being monolithically formed with the head, the extension having a maximum diameter that is less than a maximum diameter of the head.

14. A spinal implant system comprising:
a first member including an inner surface defining an implant cavity, the first member including a pair of lateral protrusions;
a second member including a head and a shaft configured to penetrate tissue, the head including a pair of longitudinal grooves, each of the grooves including one of the protrusions disposed therein, the second member including an extension extending from the head, the extension being monolithically formed with the head; and
a plurality of alternate third members, each third member being configured to directly engage the first and second members, the third members each defining an opening, the extension being configured for disposal in the openings such that the third members are interchangeable with the first and second members to form a bone fastener having a selected movement.

15. A spinal implant system as recited in claim 14, wherein the selected movement includes the second member being moveable about a plurality of axes relative to the first member.

16. A spinal implant as recited in claim 14, wherein the head is disposed within one of the openings such that rotation of the head relative to the first member causes the extension to engage an inner surface of one of the third members that defines a respective one of the openings to limit multi-axial movement of the first member relative to the second member.

17. A spinal implant comprising:
a first member including an inner surface defining an implant cavity, the first member including a pair of lateral protrusions;
a second member including a head and a shaft configured to penetrate tissue, the head including a pair of longitudinal grooves, each of the grooves including one of the protrusions disposed therein, the second member including an extension extending from the head; and
a third member directly engaging the first and second members, the third member defining an opening, the extension being disposed in the opening to restrict movement of the second member relative to the first member,
wherein the first member comprises a slot extending into the inner surface and the third member comprises a flange, the flange being received in the slot.

* * * * *